United States Patent
Miyamoto et al.

(10) Patent No.: US 12,246,184 B2
(45) Date of Patent: Mar. 11, 2025

(54) ELECTROMEDICAL DEVICE CONTROL SYSTEM, POWER SUPPLY DEVICE, RELAY DEVICE, AND POWER SUPPLY METHOD

(71) Applicant: Japan Lifeline Co., Ltd., Tokyo (JP)

(72) Inventors: Hisao Miyamoto, Tokyo (JP); Yusuke Oshima, Tokyo (JP)

(73) Assignee: JAPAN LIFELINE CO., LTD., Tokyo (JP)

( * ) Notice: Subject to any disclaimer, the term of this patent is extended or adjusted under 35 U.S.C. 154(b) by 71 days.

(21) Appl. No.: 18/166,353

(22) Filed: Feb. 8, 2023

(65) Prior Publication Data
US 2023/0264032 A1 Aug. 24, 2023

(30) Foreign Application Priority Data
Feb. 21, 2022 (JP) ................................ 2022-024610

(51) Int. Cl.
*A61B 5/00* (2006.01)
*A61N 1/378* (2006.01)

(52) U.S. Cl.
CPC .............. *A61N 1/378* (2013.01); *A61B 5/68* (2013.01)

(58) Field of Classification Search
CPC .............. A61N 1/378; A61B 5/68; A61B 5/00
USPC ............................................................ 307/11
See application file for complete search history.

(56) References Cited

U.S. PATENT DOCUMENTS

| | | | |
|---|---|---|---|
| 11,497,543 B2 | 11/2022 | Sprinkle et al. | |
| 2003/0176856 A1* | 9/2003 | Howell | A61B 90/90 606/29 |
| 2008/0125768 A1 | 5/2008 | Tahara et al. | |
| 2020/0078083 A1* | 3/2020 | Sprinkle | A61B 18/1206 |

FOREIGN PATENT DOCUMENTS

| | | |
|---|---|---|
| JP | H06-292684 A | 10/1994 |
| JP | 2001-178734 A | 7/2001 |
| JP | 2008-036390 A | 2/2008 |
| JP | 2020-517371 A | 6/2020 |

\* cited by examiner

*Primary Examiner* — Elim Ortiz
*Assistant Examiner* — Xuan Ly
(74) *Attorney, Agent, or Firm* — Muncy, Geissler, Olds & Lowe, P.C.

(57) ABSTRACT

An electromedical device control system includes a power supply device that supplies electric power to an electromedical device; and one or more relay devices that relay between the electromedical device and the power supply device. A type of the electromedical device connected to the relay device is obtained by determination using at least the relay device. The power supply device outputs the electric power in an output mode corresponding to the type of the electromedical device.

17 Claims, 9 Drawing Sheets

FIG. 4

| DETERMINATION INFORMATION 610 (BIT INFORMATION IB) | | | OUTPUT MODE OF ELECTRIC POWER Pout (CONNECTION STATUS OF RELAY DEVICE 6, TYPE OF ELECTROMEDICAL DEVICE 1) |
|---|---|---|---|
| 0 | 0 | 0 | OUTPUT MODE A (OUTPUT OF Pout ENABLED) |
| 0 | 0 | 1 | OUTPUT MODE B (OUTPUT OF Pout ENABLED) |
| 0 | 1 | 0 | OUTPUT MODE C (OUTPUT OF Pout ENABLED) |
| 0 | 1 | 1 | OUTPUT MODE D (OUTPUT OF Pout ENABLED) |
| 1 | 0 | 0 | OUTPUT MODE E (OUTPUT OF Pout ENABLED) |
| 1 | 0 | 1 | OUTPUT MODE F (OUTPUT OF Pout ENABLED) |
| 1 | 1 | 0 | OUTPUT MODE G (OUTPUT OF Pout ENABLED) |
| 1 | 1 | 1 | (RELAY DEVICE 6: NON-CONNECTED STATE) → OUTPUT OF Pout DISABLED |

| OUTPUT FORMAT | UNIPOLAR/BIPOLAR |
|---|---|
| OPERATION MODE | COAGULATION MODE/INCISION MODE |
| MAXIMUM OUTPUT ELECTRIC POWER | 50 W/100 W/200 W/OTHER |

MODIFIED EXAMPLE 1

OUTPUT MODE OF Pout CORRESPONDING TO CONTENT OF DETERMINATION INFORMATION 610A (BIT INFORMATION IB) ~ Tb'

| CONNECTION STATUS OF RELAY DEVICE 6 | | OUTPUT FORMAT/OPERATION MODE | | | CONNECTION STATUS, TYPE, AND NUMBER OF ELECTROMEDICAL DEVICES 1 | | CONNECTION STATUS/NUMBER/MAXIMUM OUTPUT ELECTRIC POWER |
|---|---|---|---|---|---|---|---|
| 0 | CONNECTED STATE (OUTPUT OF Pout ENABLED) | COAGULATION MODE (UNIPOLAR) | 0 | 0 | 0 | 0 | BOTH (1a1 AND 1a2) ARE CONNECTED |
| | | COAGULATION MODE (BIPOLAR) | 0 | 1 | 0 | 1 | ONE (1a1) IS CONNECTED (50 W MODE) |
| 1 | NON-CONNECTED STATE (OUTPUT OF Pout DISABLED) | INCISION MODE (UNIPOLAR) | 1 | 0 | 1 | 0 | ONE (1a2) IS CONNECTED (100 W MODE) |
| | | INCISION MODE (BIPOLAR) | 1 | 1 | 1 | 1 | BOTH ARE NON-CONNECTED (OUTPUT OF Pout DISABLED) |

FIG. 9

ELECTROMEDICAL DEVICE CONTROL SYSTEM, POWER SUPPLY DEVICE, RELAY DEVICE, AND POWER SUPPLY METHOD

TECHNICAL FIELD

The present disclosure relates to an electromedical device control system, a power supply device, a relay device, and a power supply method.

BACKGROUND ART

A system (electromedical device control system) for controlling an electromedical device such as an ablation catheter is disclosed, for example, in Patent Literature 1.

CITATION LIST

Patent Literature

Patent Literature 1: JP 2020-517371 T

SUMMARY OF INVENTION

Technical Problem

By the way, electromedical device control systems and the like are generally required to be made smaller and more convenient to use. It is desirable to provide an electromedical device control system, a power supply device, a relay device, and a power supply method that can improve convenience while achieving size reduction.

Solution to Problem

An electromedical device control system according to an embodiment of the present disclosure includes a power supply device configured to supply electric power to an electromedical device; and one or more relay devices configured to relay between the electromedical device and the power supply device. A type of the electromedical device connected to the one or more relay devices is obtained by determination using at least the one or more relay devices. The power supply device outputs the electric power in an output mode corresponding to the type of the electromedical device.

A power supply device according to an embodiment of the present disclosure is a power supply device configured to supply electric power to an electromedical device, the power supply device including: a power supply unit configured to output the electric power in an output mode corresponding to a type of the electromedical device connected to a relay device configured to relay between the electromedical device and the power supply device. The type of the electromedical device connected to the relay device is obtained by determination using at least the relay device.

A relay device according to an embodiment of the present disclosure is a relay device configured to relay between an electromedical device and a power supply device configured to supply electric power to the electromedical device, the relay device including: an input unit to be connected to the power supply device; an output unit to which the electromedical device is to be connected; and determination information used for determination of a type of the electromedical device connected to the output unit, the determination information defined according to the type of the electromedical device being a connection destination. The type of the electromedical device connected to the output unit is obtained by the determination using at least the relay device. The electric power output from the power supply device is output to the electromedical device being the connection destination, via the input unit and the output unit in an output mode corresponding to the type of the electromedical device.

A power supply method according to an embodiment of the present disclosure is a power supply method for supplying electric power from a power supply device to an electromedical device, the power supply method including: determining a type of the electromedical device connected to a relay device by using at least the relay device, the relay device configured to relay between the electromedical device and the power supply device; and outputting the electric power to the electromedical device in an output mode corresponding to the type of the electromedical device.

BRIEF DESCRIPTION OF DRAWINGS

FIG. 4 is a diagram illustrating an example of a truth table used for determination according to the embodiment.

FIG. 5 is a diagram illustrating an example of information included as a type of the electromedical device.

FIG. 9 is a diagram illustrating an example of a truth table used for determination according to Modified Example 1.

DESCRIPTION OF EMBODIMENTS

An embodiment of the present disclosure will be described below in detail with reference to the drawings. Note that the description will be given in the following order.

1. Embodiment (Example in which type of the connection destination electromedical device is determined using relay device)
2. Modified Examples
    Modified Example 1 (Example in which determination is made using electromedical device together with relay device)
    Modified Example 2 (example in which determination unit is provided in relay device instead of in power supply device)
3. Other Modified Examples

1. Embodiment

Overall Configuration of Electromedical Device System 5

Figure 1:
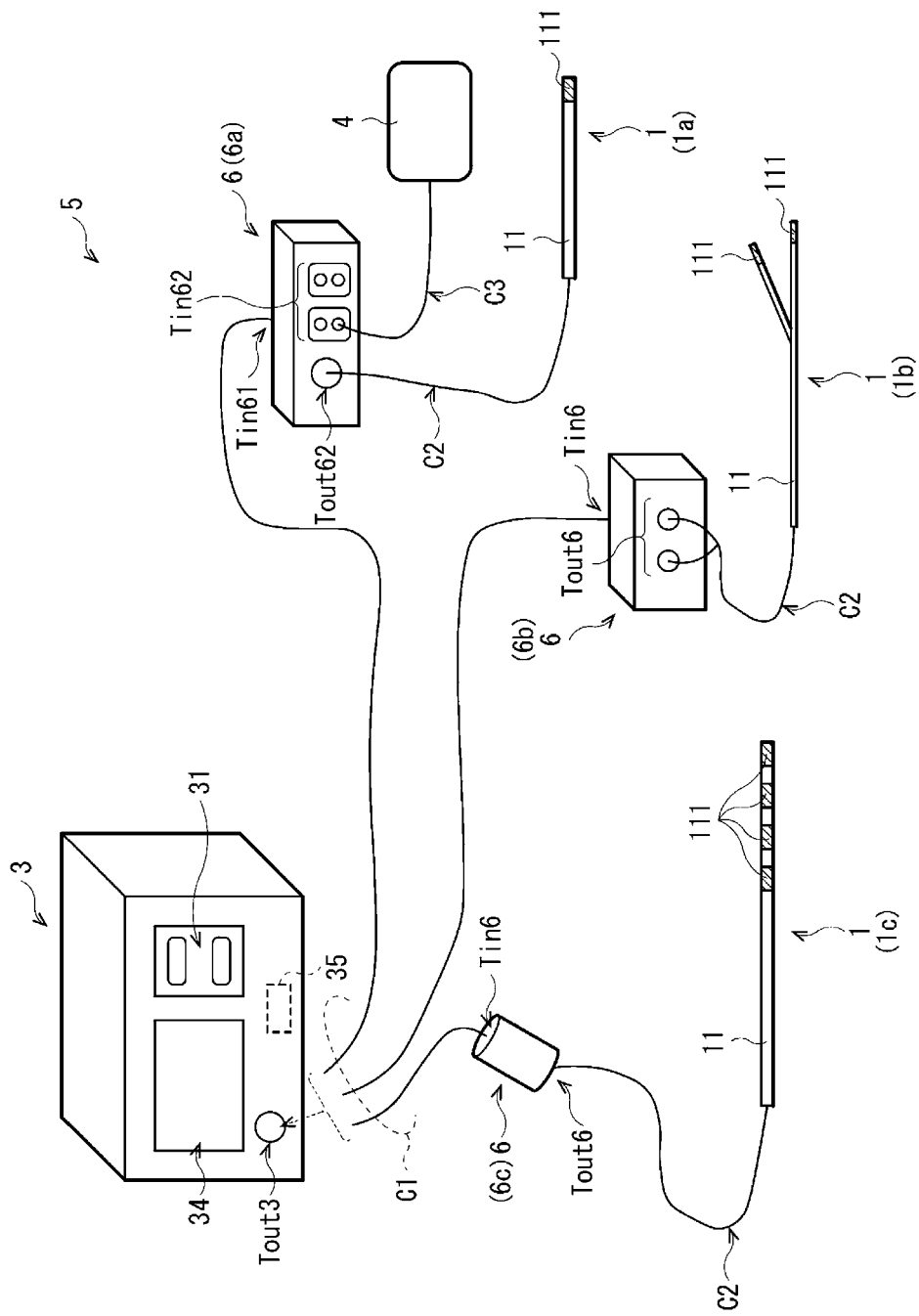
FIG. 1 is a schematic diagram illustrating an overall configuration example of an electromedical device system having an electromedical device control system according to an embodiment of the present disclosure.

FIG. 1 schematically illustrates an overall configuration example of an electromedical device system 5 according to an embodiment of the present disclosure. The electromedical device system 5 is a system used in performing a treatment or the like in a body of a patient. The treatment or the like includes treatment such as ablation (cauterization) on the affected area, incision and the like. Since the "power supply method" in the present disclosure is embodied in the electromedical device system of the present disclosure, it will be described together below.

The electromedical device system 5 includes a power supply device 3, one or more relay devices 6 (three relay devices 6a, 6b, and 6c in the example of FIG. 1), and electromedical devices 1 (three electromedical devices 1a, 1b, and 1c in the example of FIG. 1) individually connected to each relay device 6. A patient plate 4, for example, is also used as appropriate when a treatment or the like using the electromedical device system 5 is performed.

A control system configured by the power supply device 3 and the relay device 6 corresponds to a specific example of an "electromedical device control system" in the present disclosure.

Electromedical Device 1

The electromedical device 1 is a device used when performing the treatment or the like described above, and includes a device body 11 and one or more electrodes 111. The electromedical device 1 includes, for example, an ablation catheter, an electrode needle, and an electrical scalpel.

The electrode 111 is disposed near the distal end of the elongated device body 11. In the example of FIG. 1, one or more electrodes 111 are provided near the distal end of the device body 11. Specifically, in the electromedical device 1a, one electrode 111 is provided near the distal end of the device body 11. In the electromedical device 1b, the distal end side of the device body 11 is branched into two, and one electrode 111 (a total of two electrodes 111) is provided near the distal end of each branched portion. In the electromedical device 1c, a plurality of the electrodes 111 are provided near the distal end of the device body 11.

In other words, the electromedical device 1a is of a monopolar type in which treatment or the like is performed between one electrode 111 and the patient plate 4 (another electrode). Each of the electromedical devices 1b and 1c is of a bipolar type in which treatment or the like is performed between a plurality of the electrodes 111. It should be noted that, for example, a monopolar type in which treatment or the like is performed between a plurality of electrodes and a patient plate (another electrode) on the electromedical device may be used.

Relay Device 6

The relay device 6 relays between the electromedical device 1 and the like and the power supply device 3. Specifically, the relay device 6a relays between the power supply device 3 and a set including the electromedical device 1a and the patient plate 4. The relay device 6b relays between the electromedical device 1b and the power supply device 3. The relay device 6c relays between the electromedical device 1c and the power supply device 3.

The relay device 6a includes an input terminal Tin61 connected to the power supply device 3 via a connection cable C1, an output terminal Tout62 connected to the electromedical device 1a via a connection cable C2, and an input terminal Tin62 to which the patient plate 4 is connected via a connection cable C3. The relay devices 6b and 6c each include an input terminal Tin6 connected to the power supply device 3 via the connection cable C1, and an output terminal Tout6 connected to the electromedical device 1b or the electromedical device 1c via the connection cable C2. In the example of FIG. 1, one selected connection cable C1 of the three connection cables C1 individually connected to the relay devices 6a, 6b, and 6c is connected to an output terminal Tout3 (a terminal to which electric power Pout or the like is output) of the power supply device 3 as indicated by the dashed arrow. In other words, when the electromedical device 1 is used, only the relay device 6 corresponding to the electromedical device 1 to be used is connected to the power supply device 3.

For example, the output terminals Tout6 and Tout62 may have different shapes for each of the relay devices 6a, 6b, and 6c to prevent erroneous connection of the electromedical device 1 to the relay device 6.

Each of the input terminals Tin6 and Tin61 corresponds to a specific example of an "input unit" in the present disclosure. Each of the output terminals Tout6 and Tout62 corresponds to a specific example of an "output unit" in the present disclosure.

A detailed configuration example of the relay device 6 will be described later (FIGS. 2 to 5).

Power Supply Device 3

The power supply device 3 supplies electric power Pout (for example, radio-frequency (RF) electric power) for performing treatment or the like to the electromedical device 1. Specifically, the power supply device 3 supplies the electric power Pout from the output terminal Tout3 to the electromedical device 1 via the connection cable C1, the relay device 6, and the connection cable C2.

A detailed configuration example of the power supply device 3 will be described later (FIGS. 2 to 5).

Patient Plate 4

The patient plate 4 is used in a state of being attached to the body surface of a patient 9 when a treatment or the like is performed. In the example of FIG. 1, radio-frequency energization is performed (the electric power Pout is supplied) between the electrode 111 and the patient plate 4 when treatment or the like is performed using the electromedical device 1a.

Detailed Configuration of Power Supply Device 3 and Relay Device 6

Next, detailed configuration examples of the power supply device 3 and the relay device 6 will be described with reference to FIGS. 2 to 5 in addition to FIG. 1.

Figure 2:
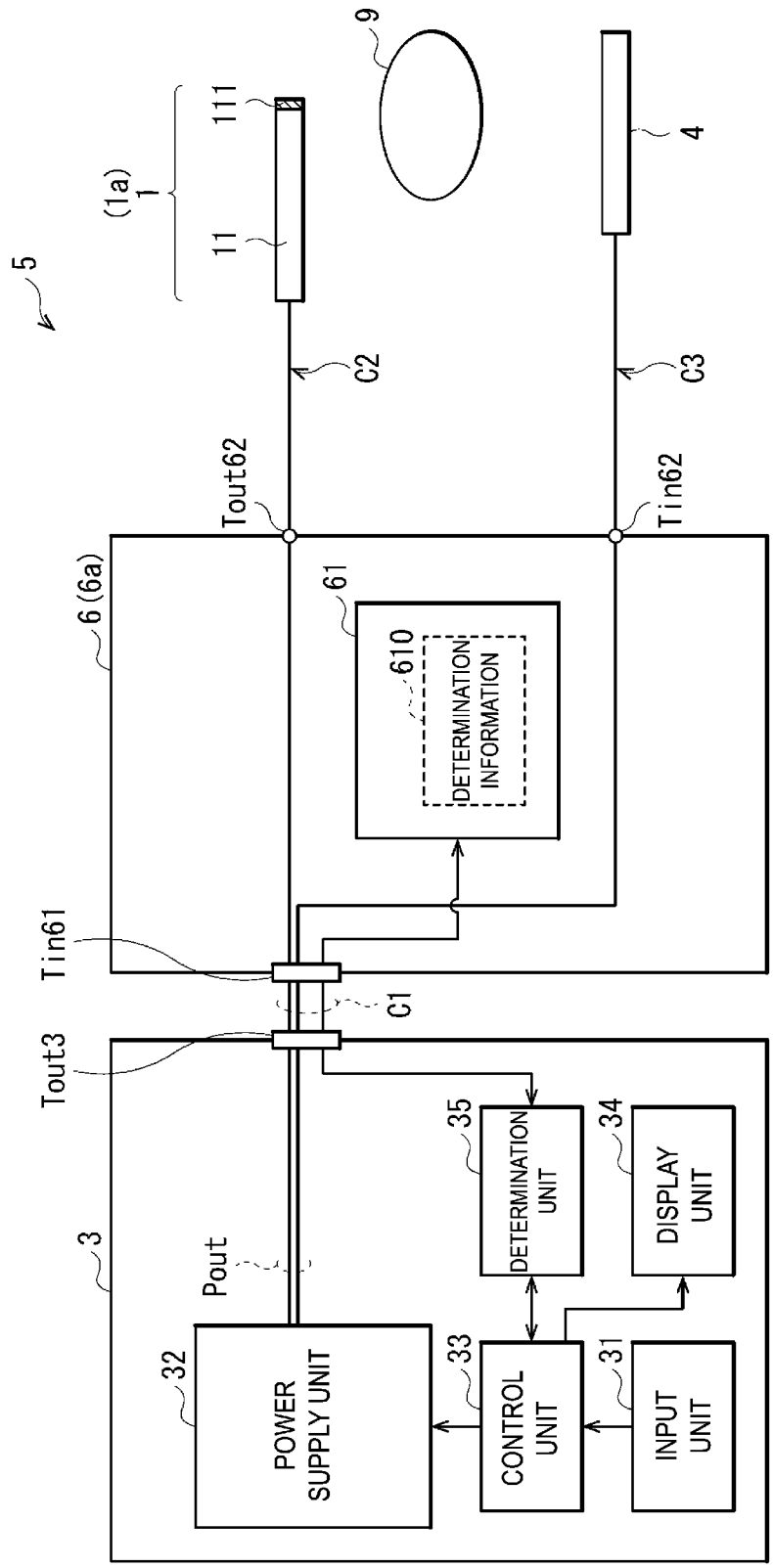
FIG. 2 is a block diagram illustrating a detailed configuration example of the electromedical device system illustrated in FIG. 1.

FIG. 2 is a block diagram illustrating an example of the detailed configuration of the electromedical device system 5 (an example in which the electromedical device 1a and the patient plate 4 are connected to the power supply device 3 via the relay device 6a).

Power Supply Device 3

The power supply device 3 includes an input unit 31, a power supply unit 32, a control unit 33, a display unit 34, and a determination unit 35, as illustrated in FIG. 2.

The input unit 31 is a portion that outputs an instruction signal (operation signal) for indicating various types of setting values or predetermined operation. The operation signal is output from the input unit 31 to the control unit 33 in response to an operation on a button or the like by an operator (for example, a technician) of the power supply device 3. However, some of the setting values may not be input according to the operation by the operator, but may be set in advance in the power supply device 3 at the time of shipment of the product, for example.

The power supply unit 32 outputs the electric power Pout according to the control by the control unit 33. The power supply unit 32 includes a predetermined power supply circuit (for example, a switching regulator). For example, when the electric power Pout is radio-frequency electric power, the frequency of the electric power Pout is approximately 450 kHz to 550 kHz (suitably 500 kHz).

The control unit 33 is a unit that controls the entire power supply device 3 and performs predetermined arithmetic processing. The control unit 33 and the determination unit 35 are configured using, for example, a microcomputer or the like. The control unit 33 controls, for example, the supply operation of the electric power Pout in the power supply unit 32 and the display operation in the display unit 34.

The display unit 34 is a unit (monitor) that displays various pieces of information and outputs these pieces of information to the outside. The display unit 34 is configured using a display according to various modes (for example, a liquid crystal display, a cathode ray tube (CRT) display, or an organic electro luminescence (EL) display).

The determination unit 35 uses the relay device 6 connected to the power supply device 3 (output terminal Tout3) to perform predetermined determination (determination regarding the type of the electromedical device 1 connected to the relay device 6). The determination unit 35 inputs and outputs various pieces of information to and from an information storage unit 61 in the relay device 6 and the control unit 33. In addition, details such as the content of determination by the determination unit 35 will be described later (FIGS. 4 and 5).

Relay Device 6

The relay device 6 (relay device 6*a*) further includes the information storage unit 61.

The information storage unit 61 stores determination information 610 that is information used for determination by the determination unit 35. The determination information 610 is defined according to the type of the (connection destination) electromedical device 1 connected to the relay device 6, and includes bit information IB defined mechanically or electrically. When the determination information 610 includes electrically defined bit information IB, the information storage unit 61 is configured using, for example, a memory (storage unit) of various storage methods. When the determination information 610 includes mechanically defined bit information IB, the information storage unit 61 and the determination information 610 are each implemented by, for example, the mechanical structure illustrated in FIG. 3 below.

Figure 3:
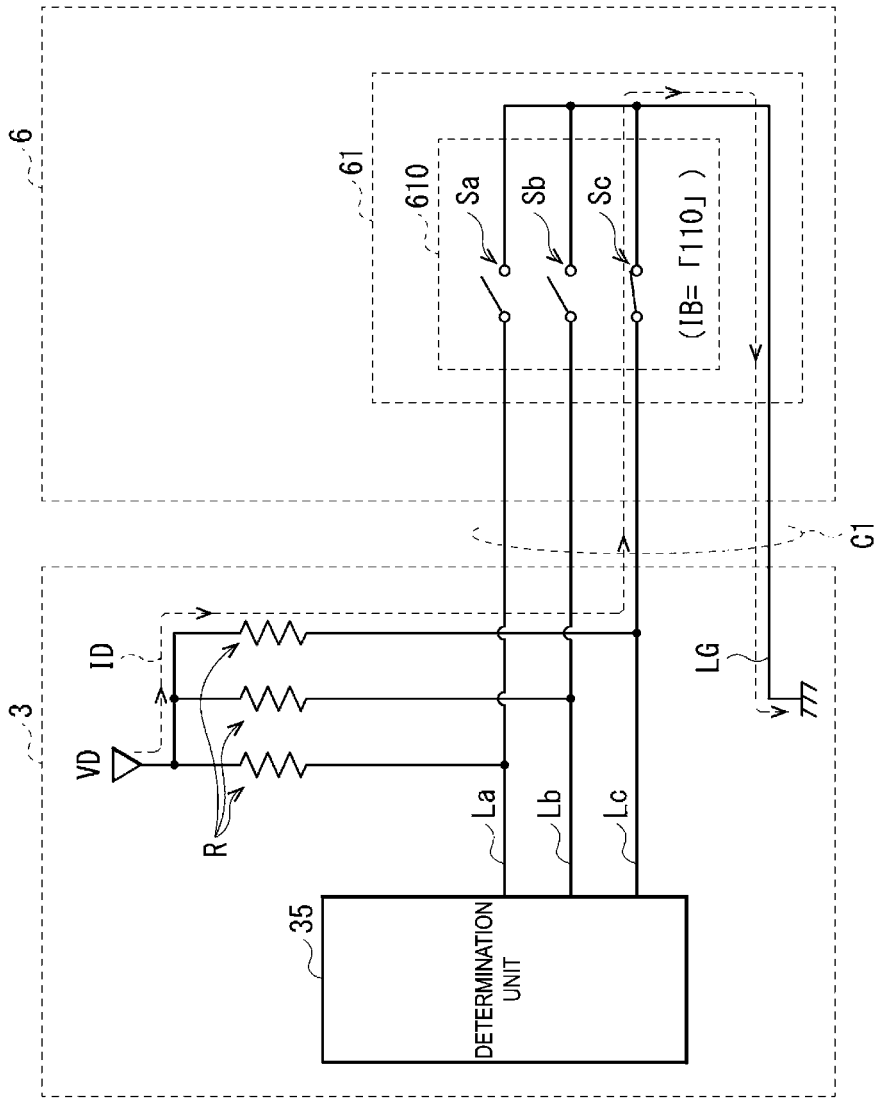
FIG. 3 is a circuit diagram selectively and schematically illustrating a detailed configuration example of a part related to determination according to the embodiment.

FIG. 3 is a circuit diagram selectively and schematically illustrating an example of detailed configuration of part related to determination according to the present embodiment (a configuration example in which the mechanically defined bit information IB is included as the determination information 610).

In the example of FIG. 3, the information storage unit 61 has three switches Sa, Sb, and Sc that constitute the determination information 610 including mechanically defined bit information IB. Specifically, information indicating the state (ON state or OFF state) of each of the switches Sa, Sb, and Sc corresponds to the bit information IB (information of each bit: "0" or "1") as the determination information 610. The switch Sa is arranged between a wire La connected to the determination unit 35 in the power supply device 3 and a wire LG connected to the ground. The switch Sb is arranged between a wire Lb connected to the determination unit 35 and the wire LG, and the switch Sc is arranged between a wire Lc connected to the determination unit 35 and the wire LG. The wires La, Lb, and Lc are individually connected to wires from a power supply VD via resistors R, respectively.

In the example of FIG. 3, the switches Sa and Sb are set to the OFF state (open state of the wire), and the switch Sc is set to the ON state (short state of the wire). As a result, as indicated by dashed arrows in FIG. 3, a current ID of a predetermined value or more (for example, a current slightly less than 1 [mA]) flows from the power supply VD to the ground via the resistor R, the wire Lc, the switch Sc, and the wire LG. On the other hand, a current ID of a predetermined value or more does not flow through the wires La and Lb and the switches Sa and Sb. Even when each of the switches Sa, Sb, and Sc is in the OFF state, a very small current less than a predetermined value (for example, a current of slightly less than 1 [μA]) flows from the power supply VD through the inside (for example, an input resistor of 10 [MΩ]) of the determination unit 35.

The determination unit 35 determines the content of the bit information IB (3-bit bit information IB in the example of FIG. 3) based on the voltage states on the wires La, Lb, and Lc. That is, when the switches Sa, Sb, and Sc are set to the ON state, since the voltage state on the wires La, Lb, and Lc is at the ground level ("L (low)" level), the determination unit 35 determines that the bit information IB of that bit is "0". When the switches Sa, Sb, and Sc are set to the OFF state, since the voltage state on the wires La, Lb, and Lc is at the power supply VD level ("H (high)" level), the determination unit 35 determines that the bit information IB of that bit is "1". Therefore, in the example of FIG. 3, when the 3-bit bit information IB is illustrated in the order of each voltage state on the wires La, Lb, and Lc, the 3-bit bit information IB is determined as "110". Note that the arrangement order of each bit is not limited to the example in FIG. 3, and can be set freely. The content of the determination information 610 including the bit information IB is individually set for each type (type of the relay device 6) of the electromedical device 1 connected to the relay device 6.

FIG. 4 illustrates an example of a truth table Tb used for determination according to the present embodiment. Specifically, the truth table Tb illustrates an example of correspondence between the content of the determination information 610 (bit information IB) and the output mode of the electric power Pout from the power supply device 3. FIG. 5 illustrates an example of information included as the type of the electromedical device 1.

In the present embodiment, the power supply device 3 (power supply unit 32) outputs the electric power Pout in an output mode corresponding to the type of the electromedical device 1 connected to the relay device 6 obtained by determination using the relay device 6 (determination by the determination unit 35). In other words, the power supply device 3 outputs the electric power Pout to the electromedical device 1 connected to each relay device 6 in a different output mode for each type of the relay device 6 (electromedical device 1). At this time, the electric power Pout output from the power supply device 3 is output to the connection destination electromedical device 1 via the input terminal (input terminal Tin6 or input terminal Tin61) and the output terminal (output terminal Tout6 or output terminal Tout62) of the relay device 6. Here, the "output mode" includes the type of the electromedical device 1 to be described later, or a setting value set by the operator within the range of the type of the electromedical device 1.

For example, as illustrated in FIG. 4, the determination unit 35 determines the connection status (connected state or non-connected state) of the relay device 6 to the power supply device 3 and the type of the electromedical device 1 connected to the relay device 6 based on the determined content of the determination information 610. For example, as illustrated in FIG. 5, the type of the electromedical device 1 includes at least one piece of information of the output format of the electromedical device 1, the operation mode when using the electromedical device 1, and the maximum output electric power of the electromedical device 1. Specific examples of the content of the output format, operation mode, and maximum output electric power are as follows, as illustrated in FIG. 5.

Output format: Unipolar type/bipolar type
Operation mode: Coagulation mode/incision mode
Maximum output electric power: 50 [W]/100 [W]/200 [W]/others A specific example of the output mode of the electric power Pout corresponding to the content of the determination information 610 (bit information IB) is as follows, as illustrated in the truth table Tb of FIG. 4. FIG. 4 also illustrates whether output of the electric power Pout is enabled in each state (IB=other than "111": Output of Pout enabled, IB="111": Output of Pout disabled). In addition, the contents such as the above-described output format, operation mode, and maximum output electric power are individually set for each of "output mode A" to "output mode G".

IB="000": Output mode A
IB="001": Output mode B
IB="010": Output mode C
IB="011": Output mode D
IB="100": Output mode E
IB="101": Output mode F
IB="110": Output mode G
IB="111": (Relay device 6: non-connected state)

Operation and Advantages and Effects

A. Basic Operation

In the electromedical device system 5, a treatment or the like is performed on the affected area of the patient 9. In performing the treatment or the like, the device body 11 is inserted into the body of the patient 9 from its distal end. The electric power Pout (for example, radio-frequency electric power) is supplied between the electrode 111 near the distal end of the device body 11 and the patient plate 4 from the power supply device 3, so that the treatment or the like by the Joule heat generation is performed on the affected area in the body of the patient 9.

By the way, in a conventional general electromedical device system, the electromedical device itself contains identification information (for example, information indicating the type of the electromedical device), and the identification information is used to determine the type (output specifications such as maximum output electric power) of the electromedical device. However, when identification information is contained in a disposable electromedical device, it may lead to an increase in cost or size of the electromedical device. Further, for example, by providing a plurality of types of connectors (electric power output terminals) in the power supply device, it is possible to prepare variations in output specifications to some extent. However, the size of the housing of the power supply device increases, the number of types of output specifications is limited by the type of the connector, and the convenience is impaired.

As described above, in a general electromedical device system, it can be said that it is difficult to improve the convenience while achieving size reduction.

B. Determination Processing and the Like

Therefore, in the electromedical device system 5 of the present embodiment, the determination unit 35 uses the relay device 6 to determine the type and the like of the connection destination electromedical device 1. In other words, in the present embodiment, such determination is performed using a non-disposable (reusable) relay device 6 instead of a disposable (single-use) electromedical device 1. Hereinafter, determination processing and the like according to the present embodiment will be described in detail with reference to FIG. 6 in addition to FIGS. 1 to 5.

Figure 6:
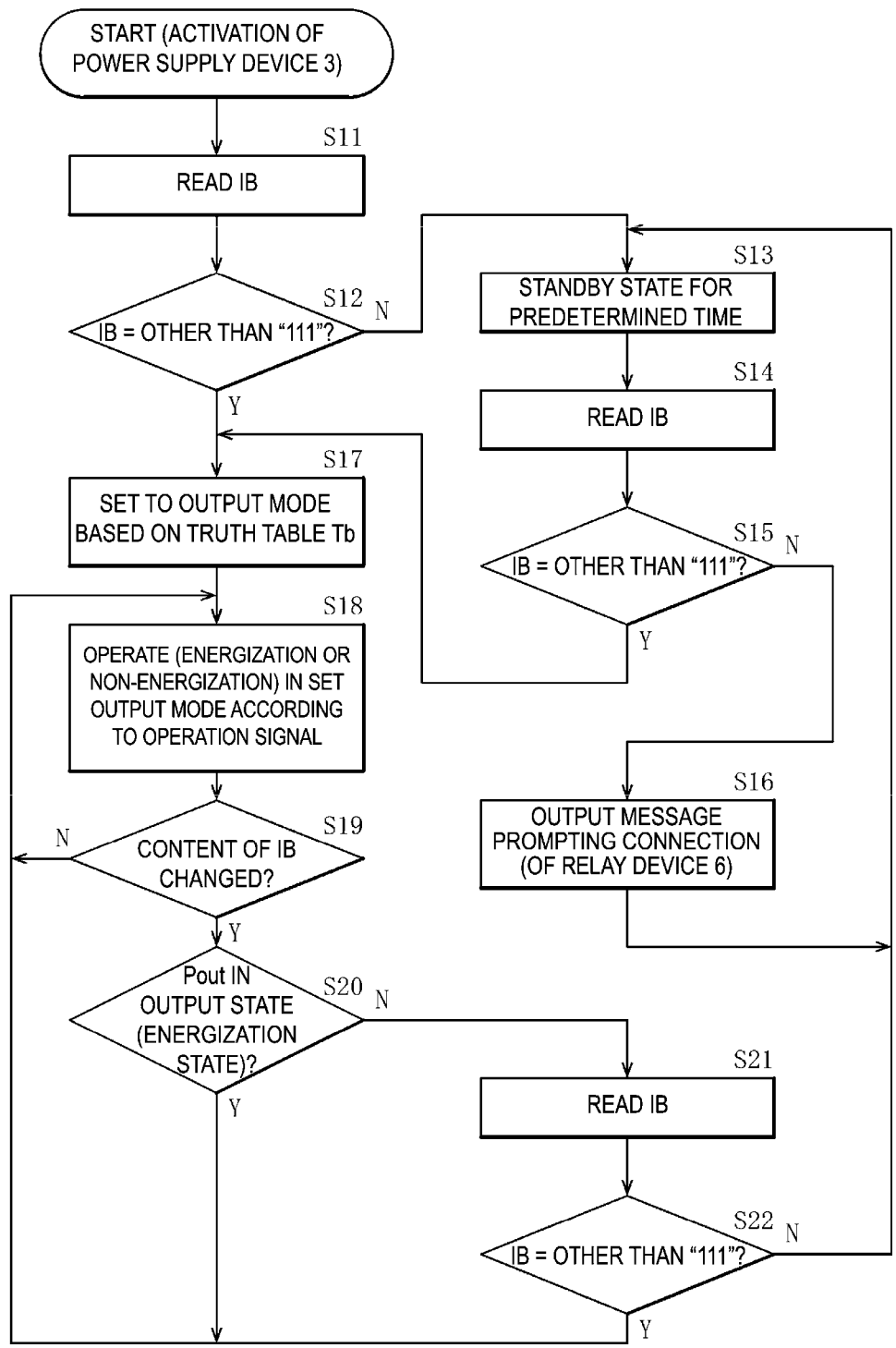
FIG. 6 is a flowchart illustrating an example of determination processing and the like according to the embodiment.

FIG. 6 is a flowchart illustrating an example of determination processing and the like according to the present embodiment.

In the series of processes illustrated in FIG. 6, when the power supply device 3 is activated, first, the determination unit 35 reads the bit information IB (determination information 610) (step S11). Next, the determination unit 35 determines whether or not the content of the read bit information IB is other than IB="111" (whether or not the relay device 6 is in the connected state) (step S12). If it is determined that IB is other than "111" (the relay device 6 is in the connected state) (step S12: Y), the process proceeds to step S17, which will be described later.

On the other hand, if it is determined that IB="111" (the relay device 6 is in the non-connected state) (step S12: N), a standby state is created for a predetermined time (for example, about several seconds) (step S13). After that, the determination unit 35 reads the bit information IB again (step S14), and determines again whether IB is other than "111" (step S15). If it is determined that IB is other than "111" (the relay device 6 is in the connected state) (step S15: Y), the process proceeds to step S17, which will be described later. On the other hand, if it is determined again that IB="111" (the relay device 6 is in the non-connected state) (step S15: N), a message prompting connection of the relay device 6 is output (for example, displayed on the display unit 34) (step S16). After that, the process returns to step S13 (standby state for predetermined time).

In step S17 described above, the determination unit 35 sets the output mode to that based on the truth table Tb according to the content of the read bit information IB (step S17). Next, the power supply device 3 (power supply unit 32) performs operation in a set output mode (energization by the output of the electric power Pout, or operation of non-energization as standby state) according to an operation signal (operator's operation) output from the input unit 31 (step S18).

Subsequently, the determination unit 35 determines whether or not the content of the bit information IB has changed thereafter (step S19). If it is determined that the content of the bit information IB has not changed (step S19: N), the process returns to step S18. On the other hand, if it is determined that the content of the bit information IB has changed (step S19: Y), the determination unit 35 determines whether or not the electric power Pout is in an output state (energized state) (step S20). This is because there is a possibility that the content of the bit information IB will change due to a noise signal during the energization in the output period (energization period) of the electric power Pout.

When it is determined that the electric power Pout is in the output state (output period) (step S20: Y), the process returns to step S18. That is, since there is a possibility that the content of the bit information IB may change due to the noise signal during the energization in the output period of the electric power Pout, the determination unit 35 does not perform determination (resetting of the output mode in step S17) based on the content of the bit information IB after the change.

On the other hand, when it is determined that the electric power Pout is not in the output state (in the output stop period) (step S20: N), the following is performed. That is, in this case, the determination unit 35 reads the bit information IB after the change (step S21), and determines whether IB is other than "111" (whether the relay device 6 is in the connected state) again (step S22). This is to determine whether or not the change in the content of the bit information IB is caused by the replacement of the relay device 6 connected to the power supply device 3 (the work of temporarily removing the relay device 6).

If it is determined that IB is other than "111" (the relay device 6 remains in the connected state) (step S22: Y), the process returns to step S18. In other words, in this case, it is determined that the change in the content of the bit information IB is not caused by the replacement of the relay device 6 (for example, the change in the content is caused by other noise signals other than during energization). Therefore, in this case as well, the determination based on the content of the bit information IB after the change (resetting of the output mode in step S17) is not performed.

On the other hand, if it is determined that IB="111" (transition to the non-connected state of the relay device 6) (step S22: N), the process proceeds to step S13 (standby state for a predetermined time). That is, in this case, it is determined that the change in the content of the bit information IB is caused by the replacement of the relay device 6 (the work of temporarily removing the relay device 6), and standby is performed until the relay device 6 after the replacement is connected to the power supply device 3. In this manner, when detecting a change in the content of the bit information IB (determination information 610) in the output stop period of the electric power Pout, the determination unit 35 performs the following. That is, after passing through the non-connected state of the relay device 6 (that is, after passing through "S22: N"→S13→S14→"S15: Y"), the determination unit 35 performs determination (step S17) based on the content of the bit information IB after the change. Also, in this case, a message prompting the connection of the relay device 6 is not output (step S16), and the process proceeds to the standby state (step S13). It should be noted that even if the relay device 6 is replaced without turning off the power and resetting, and the like, the driving of the relay device 6 is not hindered.

As a result, the series of processes illustrated in FIG. 6 ends.

C. Advantages and Effects

In this way, in the present embodiment, the electric power Pout is supplied from the power supply device 3 in an output mode corresponding to the type of the electromedical device 1 connected to the relay device 6 obtained by the determination using the relay device 6 that relays between the electromedical device 1 and the power supply device 3. In other words, the electric power Pout is supplied from the power supply device 3 to the electromedical devices 1 connected to each relay device 6 in different output modes for each type of the relay device 6 (electromedical device 1).

As a result, unlike the general electromedical device system described above, in the present embodiment, the scalability of the output mode of the electric power Pout is enhanced (variations in the output mode is ensured) while avoiding an increase in the size of the electromedical device 1 and the power supply device 3. As a result, in the present embodiment, it is possible to improve convenience while achieving size reduction.

In the present embodiment, since the determination is not performed in the output period of the electric power Pout from the power supply device 3, an erroneous determination caused by a noise signal during energization (execution of determination based on the bit information IB whose content has changed due to the noise signal during energization) can be avoided. As a result, the determination accuracy in the determination unit 35 is improved, and the convenience can be further improved.

In the present embodiment, when it is detected that the content of the determination information 610 (bit information IB) has changed in the output stop period of the electric power Pout, the determination based on the content of the determination information 610 after the change is performed only after passing through the non-connected state of the relay device 6, so that the following advantages and effects are obtained. That is, since the determination based on the content of the determination information 610 after the change is performed only when the relay device 6 connected to the power supply device 3 is replaced, erroneous determination based on the change in the content due to other noise signals other than during energization, for example, can be avoided. As a result, the determination accuracy in the determination unit 35 is improved, and the convenience can be further improved.

2. Modified Examples

Next, modified examples (Modified Examples 1 and 2) of the above-described embodiment will be described. The same components as those in the embodiment are designated by the same reference numerals, and the description thereof will be omitted as appropriate.

Modified Example 1

Configuration and Operation

Figure 7:
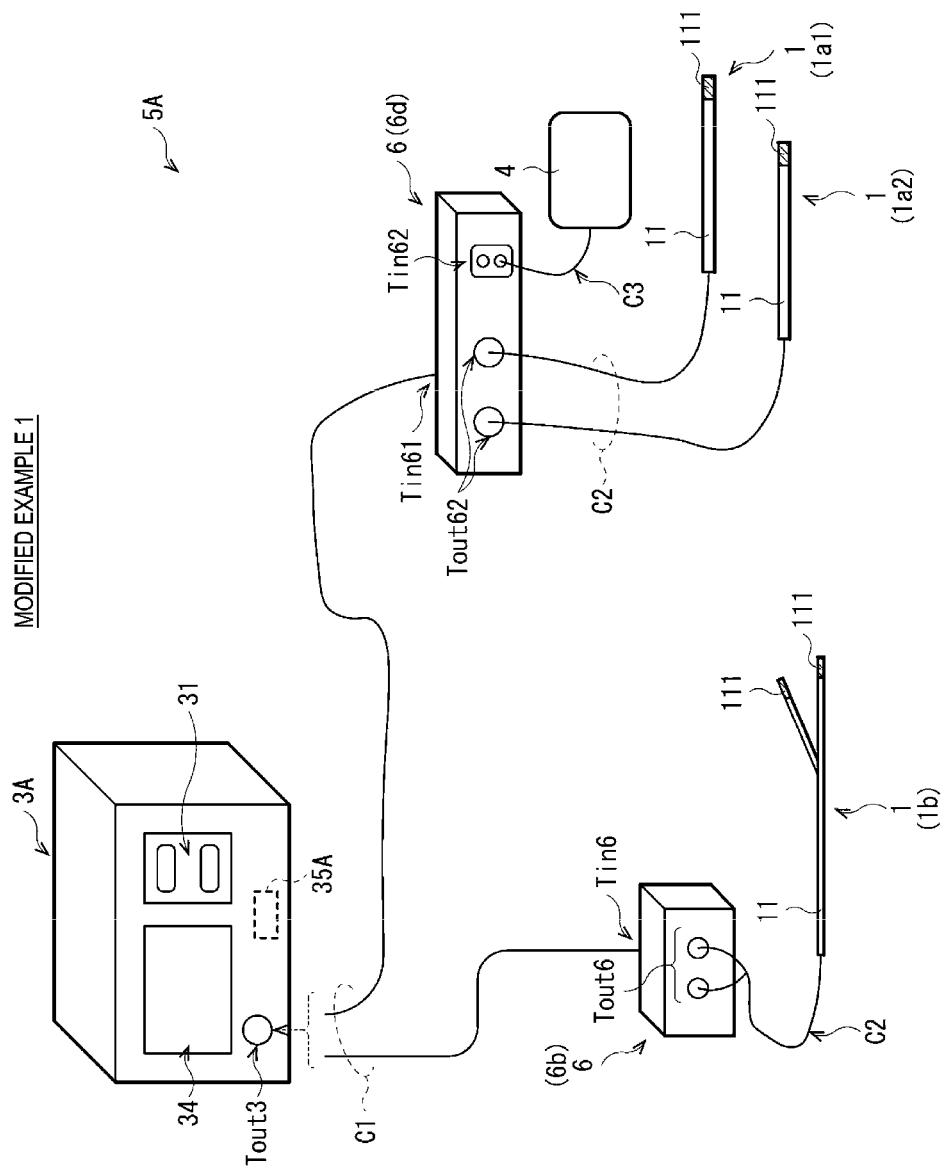
FIG. 7 is a schematic diagram illustrating an overall configuration example of an electromedical device system having an electromedical device control system according to Modified Example 1.

FIG. 7 schematically illustrates an overall configuration example of an electromedical device system 5A according to Modified Example 1. Unlike the electromedical device system 5, the electromedical device system 5A performs determination using the electromedical device 1 as well as the relay device 6, as will be described later.

The electromedical device system 5A includes a power supply device 3A, one or more relay devices 6 (two relay devices 6b and 6d in the example of FIG. 7), and electromedical devices 1 (three electromedical devices 1b, 1a1, and 1a2 in the example of FIG. 1) individually connected to each relay device 6. The patient plate 4, for example, is also used as appropriate when a treatment or the like using the electromedical device system 5A is performed.

In the example of FIG. 7, as in the example of FIG. 1, one selected connection cable C1 of the two connection cables C1 individually connected to the relay devices 6b and 6d is connected to the output terminal Tout3 (a terminal to which the electric power Pout or the like is output) of the power supply device 3A.

A control system configured by the power supply device 3A and the relay device 6 corresponds to a specific example of an "electromedical device control system" in the present disclosure.

In relay device 6d, the number of output terminals Tout62 is changed (changed from one to two) in the relay device 6a (FIG. 1). The two output terminals Tout62 are individually connected to the electromedical devices 1a1 and 1a2 via the connection cables C2. That is, only one of the two electromedical devices 1a1 and 1a2 is connected to the relay device 6d, or both of the two electromedical devices 1a1 and 1a2 are simultaneously connected to the relay device 6d.

The power supply device 3A includes a determination unit 35A instead of the determination unit 35 of the power supply device 3 (FIG. 1), and other configurations are basically the same.

Figure 8:
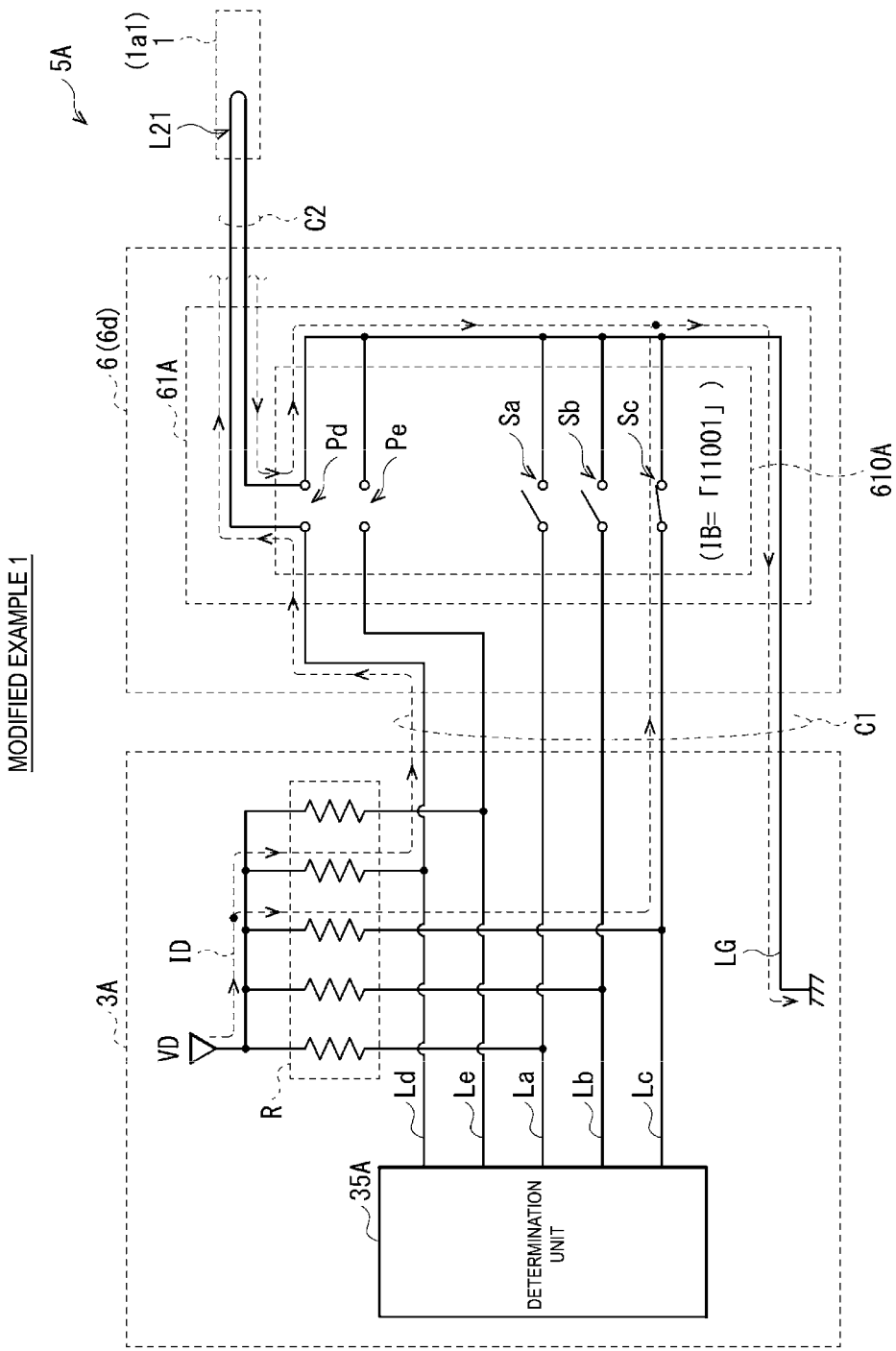
FIG. 8 is a circuit diagram selectively and schematically illustrating a detailed configuration example of a part related to determination according to Modified Example 1.

FIG. 8 is a circuit diagram selectively and schematically illustrating an example of detailed configuration of part related to determination according to Modified Example 1 (a configuration example in which the mechanically defined bit information IB is included as determination information 610A). The electromedical device system 5A illustrated in FIG. 8 illustrates an example in which the electromedical device 1a1 and the patient plate 4 are connected to the power supply device 3A via the relay device 6d.

The relay device 6d includes an information storage unit 61A having the determination information 610A instead of the information storage unit 61 having the determination information 610 in the relay device 6 (relay device 6a) illustrated in FIGS. 2 and 3.

The information storage unit 61A, similarly to the information storage unit 61, has the determination information 610A including the bit information IB. However, the information storage unit 61A has two connection pins Pd and Pe in addition to the three switches Sa, Sb, and Sc provided in the information storage unit 61. That is, the information indicating the state (ON state or OFF state) of each of the switches Sa, Sb, and Sc and each of the connection pins Pd and Pe corresponds to the bit information IB (information of each bit: "0" or "1") as the determination information 610A. The connection pin Pd is arranged between a wire Ld connected to the determination unit 35A in the power supply device 3A and the wire LG connected to the ground. The connection pin Pe is arranged between a wire Le connected to the determination unit 35A in the power supply device 3A and the wire LG.

For example, as illustrated in FIG. 8, the electromedical device 1a1 can be connected to the connection pin Pd via a wire L21 included in the connection cable C2. The electromedical device 1a2 can be connected to the connection pin Pe via the wire included in the connection cable C2. In the example of FIG. 8, the electromedical device 1a1 is connected only to the connection pin Pd of the two connection pins Pd and Pe. That is, the connection pin Pd is set to the ON state (short state of the wire), and the connection pin Pe is set to the OFF state (open state of the wire). As a result, as indicated by dashed arrows in FIG. 8, a current ID of a predetermined value or more flows from the power supply VD toward the ground via the resistor R, the wire Ld, the connection pin Pd, the wire L21, and the wire LG. On the other hand, the current ID of a predetermined value or more does not flow through the wire Le and the connection pin Pe. As in the example of FIG. 3, even when the switches Sa, Sb, and Sc or the connection pins Pd and Pe are in the OFF state, a very small current less than a predetermined value flows from the power supply VD through the inside of the determination unit 35.

The determination unit 35A determines the content of the bit information IB (5-bit bit information IB in the example of FIG. 8) based on the voltage states on the wires La to Le. That is, when the switches Sa, Sb, and Sc or the connection pins Pd and Pe are set to the ON state, since the voltage state on the wires La to Le is at the ground level ("L" level), the determination unit 35A determines that the bit information IB of that bit is "0". When the switches Sa, Sb, and Sc or the connection pins Pd and Pe are set to the OFF state, since the voltage state on the wires La to Le is at the power supply VD level ("H" level), the determination unit 35A determines that the bit information IB of that bit is "1". Therefore, in the example of FIG. 8, when the 5-bit bit information IB is illustrated in the order of each voltage state on the wires La to Le, the 5-bit bit information IB is determined as "11001". Note that the arrangement order of each bit is not limited to the example in FIG. 8, and can be set freely. The content of the determination information 610A including the bit information IB is individually set for each type (type of the relay device 6) of the electromedical device 1 connected to the relay device 6. In this manner, the determination unit 35A performs determination using the electromedical device 1 together with the relay device 6.

FIG. 9 illustrates an example of a truth table Tb' used for determination according to Modified Example 1. Specifically, the truth table Tb' illustrates an example of the output mode of the electric power Pout from the power supply device 3A according to the content of the determination information 610A (bit information IB).

The power supply device 3A outputs the electric power Pout in an output mode that is corresponding to the type of the electromedical device 1 connected to the relay device 6 and is obtained by determination using the electromedical device 1 together with the relay device 6 (determination by the determination unit 35A). In other words, the power supply device 3A outputs the electric power Pout to the electromedical device 1 connected to each relay device 6 in a different output mode for each type of the relay device 6 (electromedical device 1).

For example, as illustrated in FIG. 9, the determination unit 35A performs the following determinations based on the determined determination information 610A (bit information IB). That is, the determination unit 35A determines the connection status (connected state or non-connected state) of the relay device 6 to the power supply device 3A, the connection status of the electromedical device 1 to the relay device 6, and the type and number of electromedical devices 1 connected to the relay device 6. The type of the electromedical device 1 includes, for example, the content of the output format, operation mode, and maximum output electric power described above.

A specific example of the output mode of the electric power Pout according to the content of the determination information 610A (the content of each bit in the 5-bit bit information IB) is as follows, as illustrated in the truth table Tb' of FIG. 9. FIG. 9 also illustrates whether or not output of the electric power Pout is enabled in each state.

5th bit information="0": Connected state of relay device 6 (output of Pout enabled)

5th bit information="1": Non-connected state of relay device 6 (Output of Pout disabled)

4th and 3rd bit information="00": Coagulation mode (unipolar type)

4th and 3rd bit information="01": Coagulation mode (bipolar type)

4th and 3rd bit information="10": Incision mode (unipolar type)

4th and 3rd bit information="11": Incision mode (bipolar type)
2nd and 1st bit information="00": Connected state of two electromedical devices 1a1 and 1a2
2nd and 1st bit information="01": Connected state of one electromedical device 1a1 (50 [W] mode)
2nd and 1st bit information="10": Connected state of one electromedical device 1a2 (100 [W] mode)
2nd and 1st bit information="11": Both are non-connected (Output of Pout disabled)

When it is determined that both of the two electromedical devices 1a1 and 1a2 are in a connected state, for example, if simultaneous connection of the two devices is not permitted, it may be set such that output of the electric power Pout is disabled.

Here, in Modified Example 1 as well, as in the embodiment, the determination unit 35A does not perform determination in the output period of the electric power Pout from the power supply device 3A. Similarly, when the determination unit 35A detects that the content of the determination information 610A (bit information IB) has changed in the output stop period of the electric power Pout from the power supply device 3A, the determination unit 35A performs determination based on the content of the determination information 610A after the change after passing through the non-connected state of the relay device 6 or the electromedical device 1.

Advantages and Effects

In this manner, in Modified Example 1, the determination unit 35A performs determination using the electromedical device 1 together with the relay device 6, so that the following advantages and effects are obtained. In other words, unlike the embodiment, in Modified Example 1, it is possible to cope with a plurality of types of electromedical devices 1 while suppressing the number of relay devices 6 to one. As a result, it is possible to improve the scalability with a simpler configuration for variations in the output mode of the electric power Pout according to the determination. As a result, Modified Example 1 can further improve convenience compared to the embodiment.

In Modified Example 1, as in the embodiment, when it is detected that the content of the determination information 610A (bit information IB) has changed in the output stop period of the electric power Pout, the determination based on the content of the determination information 610A after the change is performed only after passing through the non-connected state of the relay device 6 or the electromedical device 1, so that the following advantages and effects are obtained. That is, since the determination based on the content of the determination information 610A after the change is performed only when the relay device 6 or the electromedical device 1 is replaced, erroneous determination based on the change in the content due to other noise signals other than during energization, for example, can be avoided. As a result, in Modified Example 1 as well, as in the embodiment, the determination accuracy in the determination unit 35 is improved, and the convenience can be further improved.

Modified Example 2

Figure 10:
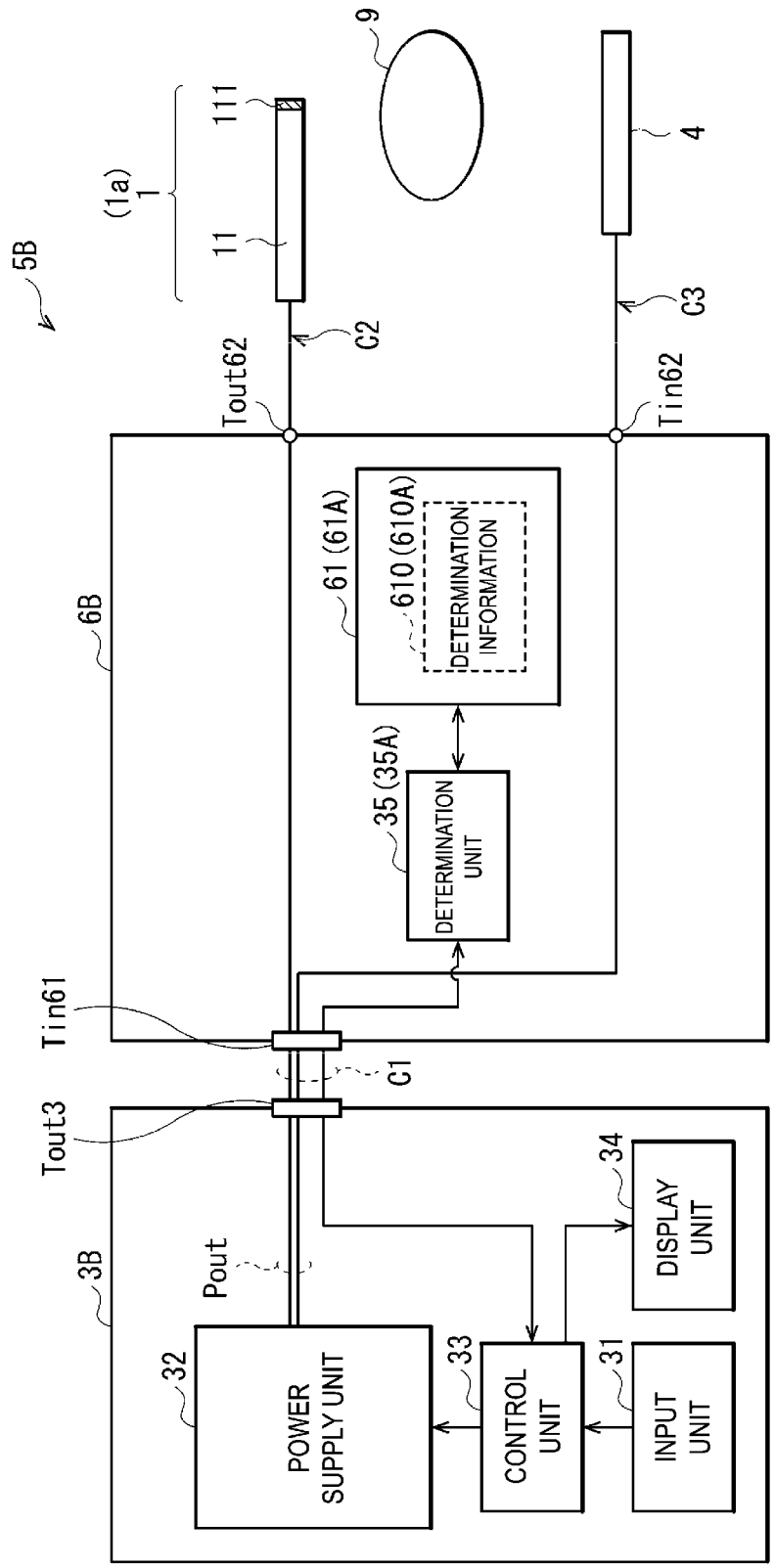
FIG. 10 is a block diagram illustrating a configuration example of an electromedical device system having an electromedical device control system according to Modified Example 2.

FIG. 10 is a block diagram of a configuration example of an electromedical device system 5B according to Modified Example 2 (an example in which the electromedical device 1a and the patient plate 4 are connected to a power supply device 3B via a relay device 6B). That is, the electromedical device system 5B includes the power supply device 3B, the relay device 6B, and the electromedical device 1a.

A control system configured by the power supply device 3B and the relay device 6B corresponds to a specific example of an "electromedical device control system" in the present disclosure.

In the electromedical device system 5B, the power supply device 3B is provided instead of the power supply device 3 in the electromedical device system 5 (FIG. 2) of the embodiment, and the relay device 6B is provided instead of the relay device 6 (relay device 6a), and other configurations are the same. Alternatively, in the electromedical device system 5B, the power supply device 3B is provided instead of the power supply device 3A in the electromedical device system 5A (FIG. 8) of Modified Example 1, and the relay device 6B is provided instead of the relay device 6 (relay device 6d), and other configurations are the same.

In the power supply device 3B, the determination unit 35 or the determination unit 35A is omitted (not provided) in the power supply device 3 (FIG. 2) or the power supply device 3A (FIG. 8), and other configurations are the same.

In the relay device 6B, the determination unit 35 or the determination unit 35A is further provided in the relay device 6a (FIG. 2) having the information storage unit 61 or the relay device 6d (FIG. 8) having the information storage unit 61A, and other configurations are the same.

As described above, in Modified Example 2, the determination unit 35 or the determination unit 35A is arranged in the relay device 6B instead of in the power supply devices 3 and 3A, respectively.

Also in Modified Example 2, basically, the same and/or similar effects as in the embodiment or Modified Example 1 can be obtained.

3. Other Modified Examples

Although the present disclosure has been described above with reference to the embodiment and the several modified examples, the present disclosure is not limited to the embodiment and the like, and various modifications are possible.

For example, in the above-described embodiment and the like, the overall configuration of the electromedical device system has been specifically described, but it is not always necessary to include all the devices, and other devices may be further included. The values, ranges, magnitude relations, and the like of various parameters described in the above-described embodiment and the like are not limited to those described in the above-described embodiment and the like, and may be other values, ranges, magnitude relations, and the like.

In the above-described embodiment and the like, an ablation device (ablation system) has been mainly described as a specific example of the electromedical device (electromedical device system), but the present disclosure is not limited to this example, and other electromedical devices (electromedical device systems) may be applied. The ablation device may be an ablation device that performs ablation using another electromagnetic wave such as a microwave or a high voltage pulse.

In the above-described embodiment and the like, an example of the case in which the determination unit is provided in the power supply device or in the relay device has been described. However, for example, the determination unit may be provided in another device (in another device different from the power supply device and the relay device).

In the above-described embodiment and the like, specific configuration examples of the information storage unit and the determination information (bit information) have been described in detail. However, the configuration examples are not limited to those described in the above-described embodiment and the like.

In the above-described embodiment and the like, the determination processing in the determination unit and the electric power output mode according to the type of the electromedical device (relay device) obtained by the determination, and the like have been specifically described. However, methods such as determination processing and electric power output modes are not limited to those described in the above-described embodiment and the like. Also, the types of electromedical devices are not limited to the types described in the above-described embodiment and the like, and other types may be used. It should be noted that, during the determination processing, for example, a high impedance state or a wire breakage state may also be detected.

The series of processes described in the above-described embodiment and the like may be performed by hardware (circuit) or software (program). When the series of processes are done by software, the software includes a group of programs for causing a computer to execute each function. Each program may be used by being preliminarily incorporated in the computer, for example, or may be installed and used in the computer from a network or a recording medium.

The various examples described so far may be applied in any combination.

Note that the effects described in the present specification are mere examples and effects of the present disclosure are not limited thereto. Other effects may be obtained.

The present disclosure may also have the following configuration.

(1)
An electromedical device control system including: a power supply device configured to supply electric power to an electromedical device; and one or more relay devices configured to relay between the electromedical device and the power supply device, wherein a type of the electromedical device connected to the one or more relay devices is obtained by determination using at least the one or more relay devices, and the power supply device outputs the electric power in an output mode corresponding to the type of the electromedical device.

(2)
The electromedical device control system according to (1), wherein the one or more relay devices have determination information used for the determination and defined according to the type of the electromedical device being a connection destination.

(3)
The electromedical device control system according to (2), wherein the determination information includes bit information defined mechanically or electrically.

(4)
The electromedical device control system according to any one of (1) to (3), further including: a determination unit configured to perform the determination using at least the one or more relay devices.

(5)
The electromedical device control system according to (4), wherein the determination unit performs the determination with respect to a connection status of the one or more relay devices to the power supply device and the type of the electromedical device connected to the one or more relay devices.

(6)
The electromedical device control system according to (4) or (5), wherein the determination unit performs the determination using the electromedical device together with the one or more relay devices.

(7)
The electromedical device control system according to (6), wherein the determination unit performs the determination using the one or more relay devices and the electromedical device with respect to: a connection status of the one or more relay devices to the power supply device; a connection status of the electromedical device to the one or more relay devices; the type of the electromedical device connected to the one or more relay devices; and the number of electromedical devices connected to the one or more relay devices.

(8)
The electromedical device control system according to any one of (4) to (7), wherein the determination unit does not perform the determination corresponding to resetting of an output mode of the electric power in an output period of the electric power from the power supply device.

(9)
The electromedical device control system according to any one of (4) to (8), wherein when the determination unit detects that a content of determination information used for the determination has changed in an output stop period of the electric power from the power supply device, the determination unit executes the determination based on the content of the determination information after the change after passing through a non-connected state of the one or more relay devices or the electromedical device.

(10)
The electromedical device control system according to any one of (4) to (9), wherein the determination unit is provided in the power supply device or the one or more relay devices.

(11)
The electromedical device control system according to any one of (1) to (10), wherein the type of the electromedical device includes at least one piece of information including: an output format in the electromedical device; an operation mode when using the electromedical device; and a maximum output electric power in the electromedical device.

(12)
A power supply device configured to supply electric power to an electromedical device, the power supply device including: a power supply unit configured to output the electric power in an output mode corresponding to a type of the electromedical device connected to a relay device configured to relay between the electromedical device and the power supply device, wherein the type of the electromedical device connected to the relay device is obtained by determination using at least the relay device.

(13)
A relay device configured to relay between an electromedical device and a power supply device configured to supply electric power to the electromedical device, the relay device including: an input unit to be connected to the power supply device; an output unit to which the electromedical device is to be connected; and determination information used for determination of a type of the electromedical device connected to the output unit, the determination information defined according to the type of the electromedical device being a connection destination, wherein the type of the electromedical device connected to the output unit is obtained by the determination using at least the relay device, and the electric power output from the power supply device is output to the electromedical device being the connection destination, via the input unit and the output unit in an output mode corresponding to the type of the electromedical device.

(14)

A power supply method for supplying electric power to an electromedical device, the power supply method including: determining a type of the electromedical device connected to a relay device by using at least the relay device, the relay device configured to relay between the electromedical device and the power supply device; and outputting the electric power to the electromedical device in an output mode corresponding to the type of the electromedical device.

(15)

An electromedical device control system including: a power supply device configured to supply electric power to an electromedical device; and one or more relay devices configured to relay between the electromedical device and the power supply device, wherein the power supply device outputs the electric power to the electromedical device connected to each of the one or more relay devices in a different output mode for respective types of the one or more relay devices.

REFERENCE SIGNS LIST 1, 1a, 1a1, 1a2, 1b, 1c Electromedical device
11 Device body
111 Electrode
3, 3A, 3B Power supply device
31 Input unit
32 Power supply unit
33 Control unit
34 Display unit
35, 35A Determination unit
4 Patient plate
5, 5A, 5B Electromedical device system
6, 6a to 6d, 6B Relay device
61, 61A Information storage unit
610, 610A Determination information
9 Patient
Pout Electric power
Tin6, Tin61, Tin62 Input terminal
Tout3, Tout6, Tout62 Output terminal
C1 to C3 Connection cable
VD Power supply
ID Current
R Resistor
La to Le, LG, L21 Wire
Sa to Sc Switch
Pd, Pe Connection pin
IB Bit information
Tb, Tb' Truth table

The invention claimed is:

1. An electromedical device control system comprising:
a power supply device configured to supply electric power to an electromedical device; and
one or more relay devices configured to relay between the electromedical device and the power supply device,
wherein a type of the electromedical device connected to the one or more relay devices is obtained by determination using at least the one or more relay devices, and
wherein the power supply device outputs the electric power via the relay devices in an output mode corresponding to the type of the electromedical device based on a result of the determination.

2. The electromedical device control system according to claim 1, wherein the one or more relay devices have determination information used for the determination and defined according to the type of the electromedical device being a connection destination.

3. The electromedical device control system according to claim 2, wherein the determination information includes bit information defined mechanically or electrically.

4. The electromedical device control system according to claim 1, further comprising:
a determination unit configured to perform the determination using at least the one or more relay devices.

5. The electromedical device control system according to claim 4, wherein the determination unit performs the determination with respect to a connection status of the one or more relay devices to the power supply device and the type of the electromedical device connected to the one or more relay devices.

6. The electromedical device control system according to claim 4, wherein the determination unit performs the determination using the electromedical device together with the one or more relay devices.

7. The electromedical device control system according to claim 1, further comprising a determination unit configured to perform the determination using the one or more relay devices and the electromedical device with respect to:
a connection status of the one or more relay devices to the power supply device;
a connection status of the electromedical device to the one or more relay devices;
the type of the electromedical device connected to the one or more relay devices; and
the number of electromedical devices connected to the one or more relay devices.

8. The electromedical device control system according to claim 4, wherein the determination unit does not perform the determination corresponding to resetting of an output mode of the electric power in an output period of the electric power from the power supply device.

9. The electromedical device control system according to claim 4, wherein when the determination unit detects that a content of determination information used for the determination has changed in an output stop period of the electric power from the power supply device, the determination unit executes the determination based on the content of the determination information after the change after passing through a non-connected state of the one or more relay devices or the electromedical device.

10. The electromedical device control system according to claim 4, wherein the determination unit is provided in the power supply device or the one or more relay devices.

11. The electromedical device control system according to claim 1, wherein the type of the electromedical device includes at least one piece of information including:
an output format in the electromedical device;
an operation mode when using the electromedical device; and
a maximum output electric power in the electromedical device.

12. A power supply device configured to supply electric power to an electromedical device, the power supply device comprising:

a power supply unit configured to output the electric power in an output mode corresponding to a type of the electromedical device connected to a relay device configured to relay between the electromedical device and the power supply device, wherein the type of the electromedical device connected to the relay device is obtained by determination using at least the relay device, and wherein the power supply unit outputs the electric power via the relay device to the electromedical device based on a result of the determination.

13. A relay device configured to relay between an electromedical device and a power supply device configured to supply electric power to the electromedical device, the relay device comprising:

an input unit to be connected to the power supply device;

an output unit to which the electromedical device is to be connected; and determination information used for determination of a type of the electromedical device connected to the output unit, the determination information defined according to the type of the electromedical device being a connection destination, wherein the type of the electromedical device connected to the output unit is obtained by the determination using at least the relay device, and wherein the electric power output from the power supply device based on a result of the determination is output to the electromedical device being the connection destination, via the input unit and the output unit in an output mode corresponding to the type of the electromedical device.

14. A power supply method for supplying electric power from a power supply device to an electromedical device, the power supply method comprising:

determining a type of the electromedical device connected to a relay device by using at least the relay device, the relay device configured to relay between the electromedical device and the power supply device; and outputting the electric power via the relay device to the electromedical device in an output mode corresponding to the type of the electromedical device based on a result of the determination.

15. The power supply device according to claim 12, further comprising a determination unit configured to performs the determination using the one or more relay devices and the electromedical device with respect to:

a connection status of the one or more relay devices to the power supply device;

a connection status of the electromedical device to the one or more relay devices;

the type of the electromedical device connected to the one or more relay devices; and the number of electromedical devices connected to the one or more relay devices.

16. A relay device according to claim 13, further comprising a determination unit configured to performs the determination using the one or more relay devices and the electromedical device with respect to:

a connection status of the one or more relay devices to the power supply device;

a connection status of the electromedical device to the one or more relay devices;

the type of the electromedical device connected to the one or more relay devices; and the number of electromedical devices connected to the one or more relay devices.

17. A power supply method according to claim 14, wherein the determining comprises determining using the relay device and the electromedical device with respect to:

a connection status of the one or more relay devices to the power supply device;

a connection status of the electromedical device to the one or more relay devices;

the type of the electromedical device connected to the one or more relay devices; and the number of electromedical devices connected to the one or more relay devices.

* * * * *